United States Patent [19]

Kwak

[11] Patent Number: 4,831,142

[45] Date of Patent: May 16, 1989

[54] SPIRO INDOLINE-PYRANOBENZOXAZINONES

[75] Inventor: Won S. Kwak, Akron, Ohio

[73] Assignee: PPG Industries, Inc., Pittsburgh, Pa.

[21] Appl. No.: 250,473

[22] Filed: Sep. 28, 1988

Related U.S. Application Data

[62] Division of Ser. No. 912,717, Sep. 26, 1986, Pat. No. 4,785,097.

[51] Int. Cl.$^4$ ............................................. C07D 498/20
[52] U.S. Cl. ...................................................... 544/71
[58] Field of Search ........................................... 544/71

[56] References Cited

U.S. PATENT DOCUMENTS

| | | | |
|---|---|---|---|
| 3,562,172 | 2/1971 | Ono et al. | 252/300 |
| 3,565,814 | 2/1971 | Pellon | 252/300 |
| 3,578,602 | 5/1971 | Ono et al. | 252/300 |
| 3,843,550 | 10/1974 | Hinnen | 252/300 |
| 4,215,010 | 7/1980 | Hovey et al. | 252/300 |
| 4,342,668 | 8/1982 | Hovey et al. | 252/586 |
| 4,634,767 | 1/1987 | Hoelscher et al. | 544/71 |

FOREIGN PATENT DOCUMENTS

| | | |
|---|---|---|
| 146135 | 6/1985 | European Pat. Off. . |
| 171909 | 2/1986 | European Pat. Off. . |
| 1927849 | 12/1970 | Fed. Rep. of Germany . |
| 1195533 | 6/1970 | United Kingdom . |
| 1416709 | 12/1975 | United Kingdom . |
| 2174711 | 11/1986 | United Kingdom . |

OTHER PUBLICATIONS

Baudisch, Science, vol. 92, No. 2839 (1940) pp. 336–337.
Baudisch, JACS, vol. 63 (1941) p. 622.
Cronheim, J. Org. Chem., vol. 12 (1947) pp. 1–6.
Cronheim J. Org. Chem., vol. 12 (1947) pp. 7–19.

*Primary Examiner*—Richard L. Raymond
*Attorney, Agent, or Firm*—Irwin M. Stein

[57] ABSTRACT

Photochromic spiro-oxizine compounds are prepared by mixing in a substantially non-reactive organic solvent medium an alkylidene heterocyclic compound or halide salt thereof, e.g., an indoline, with a metal chelate of an ortho-hydroxynitrosoaromatic compound.

5 Claims, No Drawings

SPIRO INDOLINE-PYRANOBENZOXAZINONES

This is a division of application Ser. No. 912,717, filed Sept. 26, 1986, now U.S. Pat. No. 4,785,097.

FIELD OF THE INVENTION

The present invention relates to a novel method for synthesizing spiro-oxazine compounds. More particularly, this invention relates to a method for synthesizing photochromic spiro-oxazine compounds, e.g., spiro[indoline-pyridobenzoxazine] and spiro[indoline-napthoxazine] compounds. Additionally, novel photochromic spiro-oxazine compounds, i.e., spiro[indoline-pyranobenzoxazinone] compounds are preparable by the method of this invention.

BACKGROUND OF THE INVENTION

Photochromism is a reversible phenomenon illustrated by a compound which, upon exposure to the radiation of light including ultraviolet rays, such as sunlight or the light of a mercury lamp, changes color and then returns to its original color if the radiation is discontinued or the compound is stored in the dark. A compound illustrating this phenomenon is called a "photochromic compound."

Spiro(indoline) type compounds, e.g., spiro[indoline-pyran]- and spiro[indoline-oxazine]-type compounds, have been described as possessing photochromic properties and have been suggested for use in applications in which a color change induced by sunlight is desired. For example, spiro[indoline-naphthoxazine] compounds are described in European Patent Application No. 171909 and in U.S. Pat. Nos. 3,562,172, 3,578,602, 4,215,010 and 4,342,668. Such spiro[indoline-naphthoxazine] compounds can be readily produced by the condensation reaction of an alkylidene heterocyclic compound, e.g., a Fischer's Base reactant, such as a substituted 2-methyleneindoline compound, and an ortho-nitroso-hydroxynaphthalene. Similarly, while spiro[indoline-pyran]-type compounds, such as spiro[indoline-benzopyran] or spiro[indoline-naphthopyran], can be produced respectively by the condensation reaction of a Fischer's base reactant and ortho hydroxyl formyl benzene or 1-formyl-2-hydroxylnaphthalene, efforts to obtain spiro[indoline-benzoxazine] compounds by the condensation reaction of a Fischer's base reactant and an ortho-nitrosophenol have been less successful. This lead to the search for an alternative synthetic route to compounds such as the spiro(indoline)benzoxazines.

SUMMARY OF THE INVENTION

In accordance with the present invention, a novel process of preparing spiro-oxazine compounds includes the reaction of a substituted or unsubstituted compound selected from the group consisting of 2-methyleneindoline, 2-methylenebenzoxazoline, or a halide salt thereof, e.g., the iodide salt, with a metal chelate of either a substituted or unsubstituted ortho-hydroxynitrosoaromatic compound, the aromatic compound selected from the group consisting of benzene, naphthalene, coumarin, quinoline, benzofuran, benzoxazine, isocoumarin, isoquinoline, benzoxazole, benzopyran, pyridine or chromone. For example, the process of preparing spiro[indoline-oxazine] compounds involves the reaction of an indoline (Fischer's Base) or indolium salt, e.g., the halide salt, with the metal chelate of either a substituted or unsubstituted ortho-hydroxynitrosoaromatic compound.

The metal chelate of the ortho-hydroxynitrosoaromatic compound can be prepared by mixing an aromatic or hydroxyaromatic compound with nitrous acid in the presence of, e.g., a metal salt. The nitrous acid can be prepared in situ, for example, by the admixture of sodium nitrite and an acid such as glacial acetic acid. The metal chelate includes a metal ion such as, e.g., copper, cobalt, nickel, iron, chromium, zinc, silver, palladium, mercury, gold, titanium, manganese, cadmium, platinum, zirconium, lanthanum, cerium, aluminum, lead or tin. Preferably, the metal ion is selected from among copper, cobalt, nickel, mercury, iron, zinc, lead or palladium.

By the process of the present invention, a spiro[indoline-benzoxazine] compound represented by the formula (I)

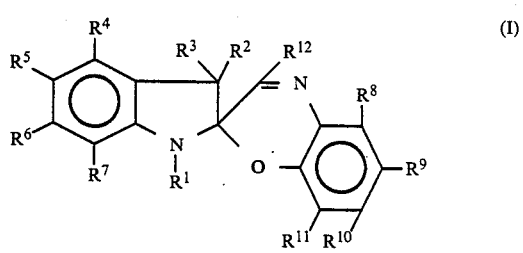

wherein $R^1$ is selected from the group consisting of $C_1$–$C_8$ alkyl, phenyl, phen($C_1$–$C_4$)alkyl, allyl and mono- or di-substituted phenyl, the phenyl substituents being selected from $C_1$–$C_4$ alkyl and $C_1$–$C_5$ alkoxy, $R^2$ and $R^3$ are each selected from the group consisting of $C_1$–$C_5$ alkyl, phenyl, mono- and di-substituted phenyl, benzyl, the phenyl substituents being selected from $C_1$–$C_4$ alkyl and $C_1$–$C_5$ alkoxy, or $R^2$ and $R^3$ combine to form a cyclic ring selected from the group consisting of a $C_6$–$C_8$ alicyclic ring, norbornyl and adamantyl, $R^4$, $R^5$, $R^6$ and $R^7$ are each selected from the group consisting of hydrogen, $C_1$–$C_5$ alkyl, halo, $C_1$–$C_5$ alkoxy, nitro, cyano, $C_1$–$C_4$ haloalkyl, $C_1$–$C_4$ polyhaloalkyl, and $C_1$–$C_8$ alkoxy carbonyl and at least one of $R^4$, $R^5$, $R^6$ and $R^7$ is hydrogen, $R^8$, $R^9$, $R^{10}$ and $R^{11}$ are each selected from the group consisting of hydrogen, $C_1$–$C_5$ alkyl, $C_1$–$C_5$ alkoxy, hydroxyl, nitro, halo, or cyano, and $R^{12}$ is selected from the group consisting of hydrogen, $C_1$–$C_5$ alkyl, $C_1$–$C_4$ alkoxy, phenyl, benzyl, pyridine or piperidine, mono- and di-substituted phenyl or benzyl, the phenyl or benzyl substituents selected from among $C_1$–$C_4$ alkyl and $C_1$–$C_5$ alkoxy, is prepared by mixing either a 2-methyleneindoline compound represented by the formula (II) or a halide salt of formula (II)

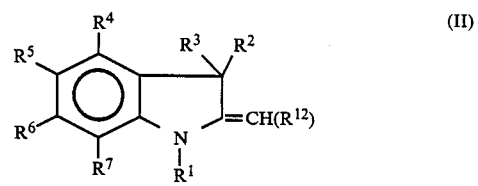

wherein $R^1$, $R^2$, $R^3$, $R^4$, $R^5$, $R^6$, $R^7$ and $R^{12}$ have their previous significance, with a metal chelate of a substituted or unsubstituted ortho-hydroxynitrosobenzene, the ortho-hydroxynitrosobenzene represented by the formula (III)

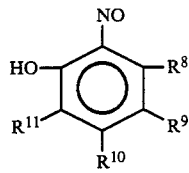

wherein $R^8$, $R^9$, $R^{10}$ and $R^{11}$ have their previous significance.

In another embodiment of the process of this invention, a spiro[indoline-naphthoxazine] compound can be prepared by mixing either a 2-methyleneindoline compound represented by formula (II) or a halide salt of formula (II) with a metal chelate of an ortho-hydroxynitrosonaphthalene, the ortho-hydroxynitrosonaphthalene represented by the formula (IV)

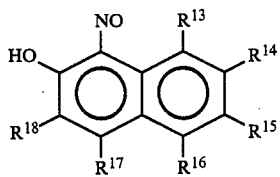

wherein $R^{13}$, $R^{14}$, $R^{15}$, $R^{16}$, $R^{17}$ and $R^{18}$ are each selected from the group consisting of hydrogen $C_1$–$C_5$ alkyl, $C_1$–$C_5$ alkoxy, hydroxyl, nitro, halo, cyano, phenyl and mono- and di-substituted phenyl with the phenyl substitutes being selected from the group consisting of $C_1$–$C_4$ alkyl or $C_1$–$C_4$ alkoxy, and at least one of $R^{13}$, $R^{14}$, $R^{15}$, $R^{16}$, $R^{17}$, and $R^{18}$ is hydrogen.

In still another embodiment of the process of this invention, a spiro[indoline-pyranobenzoxazinone] compound represented by the formula (V),

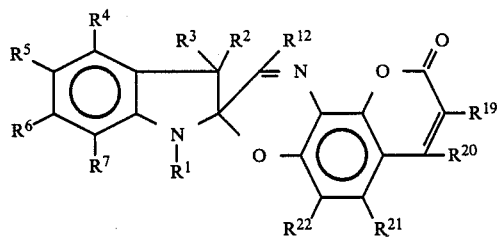

wherein $R^1$, $R^2$, $R^3$, $R^4$, $R^5$, $R^6$, $R^7$, and $R^{12}$ have their previous significance and $R^{19}$, $R^{20}$, $R^{21}$, and $R^{22}$ are each selected from the group consisting of hydrogen, $C_1$–$C_5$ alkyl, $C_1$–$C_5$ alkoxy, nitro, halo, hydroxyl, and cyano is prepared by mixing either the 2-methyleneindoline compound of formula (II) or a halide salt of formula (II) wherein $R^1$, $R^2$, $R^3$, $R^4$, $R^5$, $R^6$, and $R^7$ have their previous significance, with a metal chelate of an ortho-hydroxynitrosocoumarin, the ortho-hydroxynitrosocoumarin represented by the formula (VI)

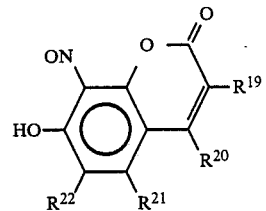

wherein $R^{19}$, $R^{20}$, $R^{21}$, and $R^{22}$ have their previous significance.

The spiro[indoline-benzoxazine] compounds represented by formula (I) are described in copending U.S. Pat. application Ser. No. 912,708, filed Sept. 15, 1986, for Photochromic Compound and Articles Containing the Same, which application was continued as Ser. No. 929,936, filed Nov. 12, 1986, which, in turn, was continued as Ser. No. 74,692, filed July 23, 1987. The spiro[indoline-pyranobenzoxazinone] compounds represented by the formula (V) are a novel class of photochromic compounds.

DETAILED DESCRIPTION OF THE INVENTION

In the present invention, a spiro-oxazine compound can be prepared by reaction of an alkylidene heterocyclic compound or a salt thereof, e.g., the halide salt of the alkylidene heterocyclic compound, and a metal chelate of an ortho-hydroxynitrosoaromatic compound. The metal ion of the metal chelate can be, e.g., copper, cobalt, nickel, iron, chromium, zinc, silver, gold, lanthanum, yttrium, palladium, mercury, titanium, manganese, cadmium, platinum, zirconium, cerium, uranium, aluminum, lead or tin. Preferably the metal chelate includes a transition metal ion such as copper, cobalt, nickel, iron, chromium, zinc, silver, gold, manganese, palladium, mercury, titanium, platinum, cadmium, and zirconium, or lead and most preferably, the metal ion is copper, iron, zinc, nickel, mercury, cobalt, lead and palladium. The ortho-hydroxynitrosoaromatic compound complexed with the metal chelate can be an aromatic compound such as, e.g., benzene, naphthalene or coumarin derivatives.

The aromatic compound can contain further substituent groups such as a $C_1$–$C_5$ alkyl, phenyl, $C_1$–$C_5$ alkoxy, halo, nitro, cyano, hydroxyl, carboxylic, thiocyano, mono- and di-substituted phenyl with the phenyl substituents being $C_1$–$C_4$ alkyl or $C_1$–$C_4$ alkoxy. The ortho-hydroxynitrosoaromatic compound can be, for example, ortho-nitroso-phenol, ortho-hydroxynitrosopyridine, substituted ortho-nitrosophenols or substituted ortho-hydroxynitrosopyridines where the substituents are selected from the group of $C_1$–$C_5$ alkyl, $C_1$–$C_5$ alkoxy, halo, nitro, phenyl, cyano, hydroxyl, thiocyano, carboxylic or mono- and di-substituted phenyl with the phenyl substituent being $C_1$–$C_4$ alkyl or $C_1$–$C_4$ alkoxy. Further, the ortho-hydroxynitrosoaromatic compound may be an ortho-hydroxynitroso derivative of a benzopyran, benzoxazine, isocoumarin, chromone, pyridine, benzoxazole, benzofuran, quinoline or iso-quinoline with or without the same substituents.

The metal chelate of an ortho-hydroxynitrosoaromatic compound can be prepared by mixing an aromatic compound or a hydroxyaromatic compound with a metal salt in the presence of nitrous acid. The nitrous acid can be generated in situ by the addition of sodium nitrite and a weak acid such as acetic acid. The reaction can be conducted, e.g., in water or a water-glacial acetic acid mixture, and the pH is maintained between about 2 and 5. The metal salt should be water soluble, e.g., the nitrate, chloride, acetate, or sulfate salt of a metal such as copper, nickel, cobalt, iron, silver, chromium, mercury, gold, titanium, zirconium, lanthanum, cerium, palladium, manganese, cadmium, zinc, platinum, aluminum, lead or tin. More preferably, the metal salt can be, e.g., copper (II) sulfate, nickel sulfate, iron (II) sulfate, cobalt (II) sulfate, zinc sulfate, palladium sulfate, copper (II) chloride, nickel chloride, iron (II) chloride, cobalt (II) chloride, zinc chloride, lead (II) chloride, palladium chloride, mercury (II) chloride, copper (II) nitrate, nickel nitrate, iron (II) nitrate, zinc nitrate, cobalt (II) nitrate, lead (II) nitrate, or mercury (II) nitrate.

The aromatic or hydroxyaromatic compound can be e.g., benzene, phenol, naphthalene, 2-naphthol, pyridine, pyridol or a heterocyclic aromatic compound, e.g., coumarin, hydroxycoumarin, isocoumarin, hydroxyisocoumarin, benzoxazole, hydroxybenzoxazole, quinoline, or quinolinol. Preferably, the aromatic or hydroxyaromatic compound is soluble in water or can be initially dissolved in a weak acid, e.g., acetic acid.

Admixture of the aromatic or hydroxyaromatic compound, the metal salt, and nitrous acid, which acid may be introduced as the combination of an acid such as acetic acid and a nitrite salt such as sodium nitrite, produces a metal complex, i.e., a metal chelate of the ortho-hydroxynitrosoaromatic compound. The pH during such a reaction is maintained at from about 2 to 5.

The alkylidene heterocyclic compound can generally be any compound represented by the formula

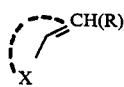

wherein X is nitrogen, oxygen or sulfur and R is a group such as hydrogen, $C_1-C_5$ alkyl or $C_1-C_5$ alkoxy. Suitable heterocyclic compounds include substituted or unsubstituted 2-methylene compounds of, e.g., indoline, benzothiazoline, or benzoxazoline. A salt, e.g., a halide salt, such as the iodide salt, of the alkylidene heterocyclic compound can be utilized to generate the 2-methylene compound reactant in situ by reaction with a base, e.g., triethylamine.

In one embodiment, a 2-methyleneindoline is selected as the alkylidene heterocyclic compound. This can provide the product, a spiro[indoline-oxazine]-type compound, with photochromic properties. For example, the indoline compound can be represented by the formula (II) previously depicted, wherein $R^1$ is $C_1-C_8$ alkyl, phenyl, phen($C_1-C_4$)alkyl, allyl or mono- and di-substituted phenyl with the phenyl substituents being $C_1-C_4$ alkyl or $C_1-C_5$ alkoxy; $R^2$ and $R^3$ are each chosen from among $C_1-C_5$ alkyl, phenyl, or mono- and di-substituted phenyl with the phenyl substituents being $C_1-C_4$ alkyl or $C_1-C_5$ alkoxy, or $R^2$ and $R^3$ combine to form a cyclic ring, e.g., an alicyclic ring containing from 6 to 8 carbon atoms, norbornyl or adamentyl; $R^4$, $R^5$, $R^6$, and $R^7$ are each selected from the group of hydrogen, a $C_1-C_5$ alkyl, $C_1-C_5$ alkoxy, halo, nitro, cyano, $C_1-C_4$ haloalkyl, $C_1-C_4$ polyhaloalkyl or $C_1-C_8$ alkoxy carbonyl, $R^{12}$ is selected from hydrogen, $C_1-C_5$ alkyl or $C_1-C_4$ alkoxy, and at least one of $R^4$, $R^5$, $R^6$ and $R^7$ is hydrogen. Such indoline compounds are commonly referred to as Fischer's bases. Preferably, $R^4$, $R^5$, $R^6$, and $R^7$ are selected from the group consisting of $C_1-C_2$ alkyl, e.g., methyl and ethyl, chlorine, bromine, and $C_1-C_2$ alkoxy, e.g., methoxy and ethoxy, $R^{12}$ is hydrogen, and at least of one $R^4$, $R^5$, $R^6$, and $R^7$ is hydrogen. Most preferably, two of $R^4$, $R^5$, $R^6$ and $R^7$ are hydrogen and the substituents other than hydrogen are present at $R^4$ and $R^5$, $R^5$ and $R^6$, $R^4$ and $R^7$, or $R^6$ and $R^7$ positions. Mixtures of indoline isomers, e.g., an isomer with $R^6$ and $R^7$ being hydrogen and $R^4$ and $R^5$ being the non-hydrogen substituents previously described, and an isomer with $R^4$ and $R^7$ being hydrogen and the $R^5$ and $R^6$ being the non-hydrogen substituents previously described, are effective in obtaining photochromic spiro[indoline]-type compounds.

In the preparation of the spiro-oxazine compound, the reaction between the metal chelate of an ortho-hydroxynitrosoaromatic compound and the alkylidene heterocyclic compound or salt thereof is conducted in a substantially non-reactive organic medium. By substantially non-reactive organic medium is meant that the organic medium undergoes a minimum amount of substitution or other reaction, preferably none, with the spiro-oxazine product. However, some solvent substitution may occur particularly at the $R^{12}$ position in the various formulae. For example, an ethoxy group may substitute at the $R^{12}$ position when ethanol is the solvent and a benzyl group may substitute when toluene is the solvent. Suitable organic mediums may include $C_1-C_5$ alkanols such as, e.g., methanol, ethanol, or isopropanol, dimethyl formamide, dimethylsulfoxide, benzene, toluene, xylene, methylene chloride, tetrahydrofuran, acetone or mixtures thereof.

The reaction conditions for the alkylidene heterocyclic compound and the metal chelate of an ortho-hydroxynitrosoaromatic compound will vary depending on the particular alkylidene heterocyclic compound, the particular metal chelate of an ortho-hydroxynitrosoaromatic compound and the organic medium. Generally, the reaction will be carried out for a period of time from about 0.1 hour to 4 hours at temperatures from about 40° C. to 140° C., preferably at temperatures from about 60° C. to 110° C. and most preferably, at or near the reflux temperature of the organic medium. The mole ratio of the alkylidene heterocyclic compound to the metal chelate of the ortho-hydroxynitrosoaromatic compound can vary generally from about 1:2 to 2:1, although preferably the mole ratio is stoichiometric.

Separation and purification of the final product, i.e., the spiro-oxazine compounds can be via crystallization using a solvent capable of dissolving the spiro-oxazine compounds, such as, e.g., n-hexane.

In one embodiment of the process of this invention, a 2-methyleneindoline compound represented by formula (II) (Fischer's base) or the iodide salt thereof is reacted with a metal, e.g., copper, chelate of an ortho-hydroxynitrosobenzene, i.e., an ortho-nitrosophenol of formula (III) to produce a class of compounds represented by the formula (I) as previously depicted where $R^1$, $R^2$, $R^3$, $R^4$, $R^5$, $R^6$, $R^7$, $R^8$, $R^9$, $R^{10}$, $R^{11}$, and $R^{12}$ have their previous significance, such compounds generally termed spiro[indoline-benzoxazine]. Preferably $R^8$, $R^9$, $R^{10}$ and $R^{11}$ are selected from among the group consisting of hydrogen, a $C_1-C_2$ alkyl, a $C_1-C_2$ alkoxyl, hydroxyl, nitro, or chloro and no more than three of $R^8$, $R^9$, $R^{10}$ and $R^{11}$ are hydrogen. More preferably, either two or three of $R^8$, $R^9$, $R^{10}$ and $R^{11}$ are hydrogen. Most preferably, the compounds prepared by this process are represented by the formula (I) wherein $R^1$ is selected from the group consisting of $C_1$–$C_4$ alkyl, phenyl or benzyl, $R^2$ and $R^3$ are each a $C_1$–$C_5$ alkyl, $R^4$, $R^5$, $R^6$ and $R^7$ are each selected from the group consisting of $C_1$–$C_2$ alkyl, hydrogen, chloro, bromo, $C_1$–$C_5$ alkoxy, $C_1$–$C_4$ haloalkyl, $C_1$–$C_4$ polyhaloalkyl, or $C_1$–$C_4$ perhaloalkyl, and at least one of $R^4$, $R^5$, $R^6$ and $R^7$ is hydrogen, and $R^8$, $R^9$, $R^{10}$ and $R^{11}$ being selected from the group consisting of hydrogen, hydroxyl, nitro, chloro, methoxy, and methyl with either two or three of $R^8$, $R^9$, $R^{10}$ and $R^{11}$ being hydrogen, and $R^{12}$ is hydrogen. Of particular interest are embodiments of formula (I) wherein $R^1$, $R^2$ and $R^3$ are methyl, $R^4$ and $R^5$ are methyl where $R^6$ and $R^7$ are hydrogen, or $R^5$ and $R^6$ are methyl where $R^4$ and $R^7$ are hydrogen, $R^8$, $R^{10}$, $R^{11}$, and $R^{12}$ are hydrogen and $R^9$ is hydroxyl, nitro, chloro or methyl.

Among the spiro[indoline-benzoxazine] compounds contemplated within the presently described structure are
6-chloro-1′,3′,3′,4′,5′-pentamethylspiro[2H-1,4-benzoxazine-2,2′-indoline],
6-chloro-1′,3′,3′,5′,6′-pentamethylspiro[2H-1,4-benzoxazine-2,2′-indoline],
6-nitro-1′,3′,3′,4′,5′-pentamethylspiro[2H-1,4-benzoxazine-2,2′-indoline],
6-nitro-1′,3′,3′,5′,6′-pentamethylspiro[2H-1,4-benzoxazine-2,2′-indoline],
6-hydroxy-1′,3′,3′,4′,5′-pentamethylspiro[2H-1,4-benzoxazine-2,2′-indoline],
6-hydroxy-1′,3′,3′,5′,6′-pentamethylspiro[2H-1,4-benzoxazine-2,2′-indoline],
1′,3′,3′,4′,5′,6-hexamethylspiro[2H-1,4-benzoxazine-2,2′-indoline], and
1′,3′,3′,5′,6′,6-hexamethylspiro[2H-1,4-benzoxazine-2,2′-indoline].

In another embodiment of this invention, a 2-methyleneindoline compound represented by formula (II) or the iodide salt thereof is reacted with a metal chelate of an ortho-hydroxynitrosonaphthalene, i.e., an ortho-nitrosonaphthol of formula (IV) to produce a class of compounds generally termed spiro[indoline-naphthoxazines]. In such compounds. $R^1$–$R^7$ and $R^{12}$–$R^{18}$ have their previously described significance. Preferably, $R^{13}$–$R^{18}$ are selected from the group consisting of hydrogen, a $C_1$–$C_2$ alkyl, a $C_1$–$C_2$ alkoxy, hydroxyl, nitro or chloro and at least three of $R^{13}$–$R^{18}$ are hydrogen. For example, $R^{13}$, $R^{16}$ and $R^{17}$ may be hydrogen and $R^{14}$, $R^{15}$ and $R^{18}$ selected from among $C_1$–$C_2$ alkyl, $C_1$–$C_2$ alkoxy, hydroxyl, nitro, and chloro. Most preferably in the compounds prepared by this process, $R^1$ is selected from the group of $C_1$–$C_4$ alkyl, phenyl or benzyl, $R^2$ and $R^3$ are each a $C_1$–$C_5$ alkyl, $R^4$, $R^5$, $R^6$ and $R^7$ are each selected from among $C_1$–$C_2$ alkyl, hydrogen, chloro, bromo, $C_1$–$C_5$ alkoxy, $C_1$–$C_4$ polyhaloalkyl, $C_1$–$C_4$ haloalkyl or $C_1$–$C_4$ perhaloalkyl, and at least one of $R^4$, $R^5$, $R^6$ and $R^7$ is hydrogen, and $R^{13}$–$R^{18}$ are selected from the group consisting of hydroxy, nitro, chloro, methoxy and methyl and at least three of $R^{13}$–$R^{18}$ are hydrogen and $R^{12}$ is hydrogen.

In still another embodiment of this invention, a 2-methyleneindoline compound represented by formula (II) or the iodine salt thereof is reacted with a metal, e.g., copper chelate of an ortho-hydroxynitrosocoumarin of formula (VI) to produce a class of compounds generally termed spiro[indoline-pyranobenzoxazinones]. In such compounds, $R^1$–$R^7$, $R^{12}$ and $R^{19}$–$R^{22}$ have their previously described significance. Preferably $R^{19}$–$R^{22}$ are selected from the group consisting of hydrogen, a $C_1$–$C_2$ alkyl, a $C_1$–$C_2$ alkoxy, hydroxyl, nitro or chloro and either two or three of $R^{19}$–$R^{22}$ are hydrogrm. For example, $R^{19}$, $R^{21}$ and $R^{22}$ can be hydrogen and $R^{20}$ can be methyl. The left side of this spiro[indoline] compound is most preferably the same as described for the spiro[indoline-benzoxazine]. Examples of the compounds preparable by this process are the compounds of formula (V) wherein $R^1$, $R^2$, and $R^3$ are methyl, $R^4$ and $R^5$ are methyl where $R^6$ and $R^7$ are hydrogen, or $R^5$ and $R^6$ are methyl where $R^4$ and $R^7$ are hydrogen, $R^{12}$ is hydrogen, ethoxy or benzyl, $R^{19}$, $R^{22}$ and $R^{21}$ are hydrogen and $R^{20}$ is methyl, methoxy or chloro.

Among the spiro[indoline-pyranobenzoxazinone] compounds contemplated within the presently described structure are
1,3,3,5,6,7′-hexamethylspiro[indoline-2,3′-[3H,9H]pyrano[2,3-f][1,4]benzoxazin]-9′-one,
1,3,3,4,5,7′-hexamethylspiro[indoline-2,3′-[3H,9H]pyrano[2,3-f][1,4]benzoxazin]-9′-one,
7′-methoxy-1,3,3,4,5-pentamethylspiro[indoline-2,3′-[3H,9H]pyrano[2,3f]-[1,4]benzoxazin]-9′-one, and
7′-methoxy-1,3,3,5,6-pentamethylspiro[indoline-2,3′-[3H,9H]pyrano[2,3f]-[1,4]benzoxazin]-9′-one Other spiro-oxazine compounds may be prepared in a similar manner to the spiro[indoline-benzoxazine], spiro[indoline-napthoxazine] and spiro[indoline-pyranobenzoxazinone] compounds by changing the alkylidene heterocyclic compound and the ortho-hydroxynitrosoaromatic compound. For example, spiro[indoline-pyridobenzoxazine] compounds and spiro[indoline-pyridooxazine] compounds may be prepared by reacting the indoline compounds (Fischer's base) as previously described with metal chelates of ortho-hydroxynitrosoquinoline or ortho-hydroxynitrosopyridine. Similarly, other alkylidene heterocyclic compounds such as 2-ethylidine indoline (Fischer's base) are contemplated as being reacted with the metal chelates of, e.g., ortho-nitrosophenol.

The spiro[indoline-benzoxazine] compounds and spiro[indoline-pyranobenzoxazinone] compounds possess photochromic properties. These photochromic compounds can be incorporated into synthetic plastic materials such as polymers and copolymers of polyol(allyl carbonate) monomers, polyacrylates, poly(alkylacrylates) such as polymethylmethacrylates, cellulose acetate, cellulose propionate, cellulose butyrate, cellulose triacetate, cellulose acetate propionate, cellulose acetate butyrate, poly(vinyl acetate), poly(vinyl alcohol), polyurethanes, polycarbonates, polyethyleneterephthalate, polystyrene, poly(styrene-methylmethacrylate) copolymers, poly(styrene-acrylonitrile) copolymers, polyvinyl pyrrolidone, polyvinyl chloride, polyvinyl butyrate and polyvinyl butyral. Transparent blends of the transparent polymers and copolymers are also suitable as hot materials. Preferably, the material is an optically clear polymerized organic material prepared from a polycarbonate, such as poly(4,4′-dioxydiphenol-2,2-propane), which is sold under the trademark, Lexan; a polyol(allyl carbonate), especially polymers of diethylene glycol bis(allyl carbonate), which is sold under the trademark CR-39, and its copolymers with, for example, vinyl acetate, e.g., copolymers of from 80–90 percent diethylene glycol bis(allyl carbonate) and 10–20 percent vinyl acetate, particularly 80–85 percent of the bis(allyl carbonate)

and 15-20 percent vinyl acetate; cellulose acetate, cellulose propionate, cellulose butyrate; polystyrene and its copolymers with methyl methacrylate, vinyl acetate and acrylonitrile, and cellulose acetate butyrate. Preferably, the synthetic plastic material is an optically clear material, i.e., a material suitable for ophthalmic or optical elements such as lenses, windows or windshields.

The present invention is further illustrated by the following examples. Obviously, many modifications and variations of the present invention are possible in light of this specification. Therefore, it should be understood that while the invention is described herein with specific details relating to certain embodiments, the invention may be practiced otherwise than as specifically described and yet within the scope of the appended claims.

EXAMPLE 1

A 1-nitroso-2-hydroxynaphthalene copper (II) complex was prepared as follows. In 75 milliliters (ml) of a 1:1:1 by volume mixture of glacial acetic acid, ethanol and water was dissolved 7.2 grams (g) of 2-naphthol (0.05 mole). The solution was adjusted to pH of 4.2 with sodium acetate (4.4 g). In a second vessel, 4.78 g of copper sulfate (0.03 mole) was dissolved in 150 ml of water. As 5.18 g of sodium nitrite (0.075 mole) was added with stirring to the copper solution, the solution turned dark green. This dark green solution was added to the 2-naphthol solution with vigorous mixing while maintaining the reaction solution pH at from 4.1 to 4.3 by addition of an additional 4.85 g of sodium acetate. A brown powder was formed almost immediately. The suspension of brown powder was stirred for 5 to 10 minutes, then the brown powder was filtered, washed with water and air-dried. A total of 9.8 g of the brown powder was obtained. An IR analysis showed similar peaks to that of 1-nitroso-2-napthol.

EXAMPLE 2

The brown powder from Example 1 (2.04 g, 0.01 mole) was suspended in 40 ml of ethanol. Carbon dioxide gas was bubbled through the reaction vessel during the reaction. The suspension was heated to reflux with vigorous stirring. To the hot suspension was added 3.29 g of 1,2,3,3,4,5(or 1,2,3,3,5,6)-hexamethylindolium iodide (0.01 mole) dissolved in 30 ml of ethanol with 1.2 g of triethylamine (0.012 mole). The reaction mixture was refluxed for 3 hours, and the filtered through a coarse sintered glass funnel while hot. The filtrate was reduced to a small volume using a rotorvap system and then allowed to evaporate in the air. The product, a powder, was collected by filtration and then air dried. The powder was treated with boiling n-hexane and filtered to separate n-hexane-soluble materials. The filtrate was evaporated and the powder collected, washed with ethanol and air-dried. Total yield was 2.36 g. Characterization of the product by mass spectrometry indicated a molecular weight of 356. IR and proton NMR data were identical to those of the known compound
1,3,3,4(or 6),5-pentamethylspiro[[3H]-[1,4]-napthoxazine-2,3'-indoline].
A portion of the powder dissolved in ethanol turned blue and in toluene turned purplish blue upon exposure to ultraviolet light and the colors faded completely when placed in the dark.

EXAMPLE 3

A 4-methyl-8-nitroso-7-hydroxycoumarin copper (II) complex was prepared as follows. In 200 ml of a 1:1 by volume mixture of glacial acetic acid and water was suspended 8.8 g of 4-methyl-7-hydroxycoumarin (0.05 mole). The suspension was adjusted to a pH from 4.0 to 4.5 with about 50 g of sodium acetate. To this suspension was added solution of 4.0 g copper sulfate (0.025 mole) and 8.7 g sodium nitrite (0.125 mole) in 200 ml of water. More sodium acetate was added (about 10 g) to adjust the pH of the suspension to about 4.5. The reaction mixture was heated at 70° C. to 75° C. in a water bath for 2 to 3 hours whereupon the mixture turned dark purple. This mixture was cooled to room temperature. Upon filtration, a grey to black powder was collected, washed with water and air-dried. The powder was suspended in 250 ml of boiling acetone and filtered. An acetone insoluble black powder was collected, washed with fresh acetone and air-dried.

EXAMPLE 4

The acetone-insoluble black powder (1.18 g) from Example 3 was slowly added over about 15 minutes to a hot ethanol solution (50 ml) containing 1.64 g of 1,2,3,3,4,5(or 5,6)-hexamethylindolium iodide and 0.51 g of triethylamine. This reaction mixture was refluxed for 2.5 hours and then evaporated at room temperature to yield a dark hard paste. This dried paste was treated with several portions of boiling n-hexane (about 400 ml total) and filtered. The filtrates were combined, treated with anhydrous magnesium sulfate, filtered and then reduced in volume to about 10 ml with gentle heating. As the solution, dark red wine in color, was cooled in an ice bath, a dark orange powder was formed. The powder was collected, washed with n-hexane and air-dried. Additional powder was obtained from the filtrate, washed, dried and combined with the rest to yield about 72 milligrams. A portion of the powder in either ethanol or toluene turned from yellow to green when exposed to ultraviolet light and then bleached to the original pale yellow in the dark at room temperature. Characterization of the product by mass spectrometry indicated two major species with molecular weights of 432 and 388 corresponding to the compounds
1,3,3,4(and 6),5,7'-hexamethylspiro[indoline-2,3'-[3H,9H]pyrano[2,3-f]-[1,4]benzoxazin]-9'-one and 2'-ethoxy-1,3,3,4(and 6),5,7'-hexamethyl-spiro[indoline-2,3'-[3H,9H]pyrano[2,3-f]-[1,4]benzoxazin]-9'-one. The $^1$H NMR indicated the presence of an ethoxy thereby suggesting at least some product had been ethoxylated by the solvent, a result supported by spectrometry results.

EXAMPLE 5

A procedure similar to Example 4 was followed except toluene was used in place of ethanol. The resultant powder had a mass spectrometry results indicating a molecular weight of 388 as expected.

EXAMPLE 6

In 20 ml of glacial acetic acid was dissolved 6.96 g of 4-nitrophenol (0.05 mole). This solution was diluted with 40 ml of water and the pH was adjusted to from 4.0 to 4.5 with 47 g of sodium acetate. In a second vessel, 4.78 g of copper sulfate (0.03 mole) and 5.18 g of sodium nitrite (0.075 mole) was dissolved in 150 ml of water. The dark green copper sulfate-sodium nitrite reaction solution was added to the 4-nitrophenol solution while maintaining the solution pH at from 4.0 to 4.5 by addition of sodium acetate. As no significant reaction had occurred, a second copper sulfate-sodium nitrite solution was prepared and added to the previous mixture. Then, the reaction mixture was vigorously stirred and brought to boiling. After boiling for about 2 to 3 minutes, the resultant dark purple solution was allowed to cool to room temperature. A small amount of powder was recovered, washed with water and methanol, and then air-dried. An almost black powder (0.5 g) was obtained.

EXAMPLE 7

The black powder (0.5 g) from example 6 was added in small portions over about 5 to 10 minutes to a suspension of 1.0 g of 1,2,3,3,4,5(or 1,2,3,3,5,6)-hexamethylindolium iodide in 30 ml of hot toluene. During the addition, the suspension initially turned green and then dark red-purple. The reaction mixture was heated at the reflux temperature for about 10 minutes and then filtered while hot. The filtrate volume was reduced under vacuum and air-dried at room temperature. The dry residue was treated with several portions of hot n-hexane (about 200 ml). The n-hexane extracts were combined and then reduced in volume by evaporation to less than 10 ml. A yellow-orange powder was collected, washed with n-hexane and air-dried. Mass spectrometry indicated a major component with a molecular weight of 351 corresponding to the compound 7-nitro-1′,3′,3′,4′(and 6′),5′-pentamethylspiro[2H-1,4]benzoxazine-2,2′-indoline] and a minor component with a molecular weight of 441 corresponding to the compound with a substituted benzyl group from the solvent, i.e., 3-benzyl-7-nitro-1′,3′,3′,4′(and 6′),5′-pentamethylspiro[2H-1,4-benzoxazine-2,2′-indoline]. A portion of the powder in either toluene or ethanol turned from pale yellow to green upon exposure to ultraviolet light and faded to the pale yellow color when kept in the dark.

I claim:

1. A compound represented by the formula:

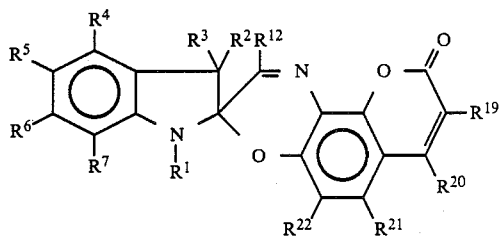

wherein $R^1$ is selected from the group consisting of $C_1$–$C_8$ alkyl, phenyl, phen($C_1$–$C_4$)alkyl, allyl and mono- or di-substituted phenyl, the phenyl substituents being selected from $C_1$–$C_4$ alkyl and $C_1$–$C_5$ alkoxy; $R^2$ and $R^3$ are each selected from the group consisting of $C_1$–$C_5$ alkyl, phenyl, mono- and di-substituted phenyl, and benzyl, the phenyl substituents being selected from $C_1$–$C_4$ alkyl and $C_1$–$C_5$ alkoxy, or $R^2$ and $R^3$ combine to form a cyclic ring selected from the group consisting of a $C_6$–$C_8$ alicyclic ring, norbornyl and adamantyl; $R^4$, $R^5$, $R^6$ and $R^7$ are each selected from the group consisting of hydrogen, $C_1$–$C_5$ alkyl, halogen, $C_1$–$C_5$ alkoxy, nitro, cyano, $C_1$–$C_4$ haloalkyl, $C_1$–$C_4$ polyhaloalkyl, and $C_1$–$C_8$ alkoxy carbonyl, provided that at least one of $R^4$, $R^5$, $R^6$, and $R^7$ is hydrogen; $R^{19}$, $R^{20}$, $R^{21}$ and $R^{22}$ are each selected from the group consisting of hydrogen, $C_1$–$C_5$ alkyl, $C_1$–$C_5$ alkoxy, hydroxyl, nitro, halogen, and cyano, and $R^{12}$ is hydrogen.

2. The compound of claim 1 wherein $R^1$, $R^2$, $R^3$, $R^4$, and $R^5$ are each methyl, $R^6$ and $R^7$ are hydrogen, $R^{19}$, $R^{21}$ and $R^{22}$ are hydrogen and $R^{20}$ is methyl.

3. The compound of claim 1 wherein $R^1$, $R^2$, $R^3$, $R^5$ and $R^6$ are each methyl, $R^4$ and $R^7$ are hydrogen, $R^{19}$, $R^{21}$ and $R^{22}$ are hydrogen and $R^{20}$ is methyl.

4. The compound of claim 1 wherein $R^1$, $R^2$, $R^3$, $R^4$ and $R^5$ are each methyl, $R^6$ and $R^7$ are hydrogen, $R^{19}$, $R^{21}$ and $R^{22}$ are hydrogen, and $R^{20}$ is methoxy.

5. The compound of claim 1 wherein $R^1$, $R^2$, $R^3$, $R^5$ and $R^6$ are each methyl, $R^4$ and $R^7$ are hydrogen, $R^{19}$, $R^{21}$ and $R^{22}$ are hydrogen and $R^{20}$ is methoxy.

* * * * *